United States Patent
Kamenoue

(10) Patent No.: US 10,968,170 B2
(45) Date of Patent: Apr. 6, 2021

(54) VISCOMETRIC PROPERTIES IMPROVER

(71) Applicant: KAO CORPORATION, Tokyo (JP)

(72) Inventor: Shogo Kamenoue, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/098,999

(22) PCT Filed: May 9, 2017

(86) PCT No.: PCT/JP2017/017512
§ 371 (c)(1),
(2) Date: Nov. 5, 2018

(87) PCT Pub. No.: WO2017/203967
PCT Pub. Date: Nov. 30, 2017

(65) Prior Publication Data
US 2019/0152904 A1 May 23, 2019

(30) Foreign Application Priority Data
May 25, 2016 (JP) .............................. JP2016-104190

(51) Int. Cl.
*C09K 5/20* (2006.01)
*C07C 305/10* (2006.01)
*C09K 5/10* (2006.01)
*F01P 3/20* (2006.01)
*F01P 3/00* (2006.01)

(52) U.S. Cl.
CPC .............. *C07C 305/10* (2013.01); *C09K 5/10* (2013.01); *C09K 5/20* (2013.01); *F01P 3/00* (2013.01); *F01P 3/20* (2013.01); *F01P 2003/001* (2013.01)

(58) Field of Classification Search
CPC .................................. C09K 5/00; C09K 5/20
USPC ..................................................... 252/75, 78
See application file for complete search history.

(56) References Cited

U.S. PATENT DOCUMENTS

| | | | | |
|---|---|---|---|---|
| 4,692,271 A | * | 9/1987 | Messenger | C11D 1/645 510/417 |
| 5,057,241 A | * | 10/1991 | Merritt | C11D 3/225 510/119 |
| 6,313,085 B1 | * | 11/2001 | Le Hen-Ferrenbach | A61K 8/463 510/424 |
| 2004/0069342 A1 | | 4/2004 | Hellsten et al. | |
| 2010/0160206 A1 | * | 6/2010 | Chiba | A61K 8/86 510/467 |
| 2015/0211407 A1 | | 7/2015 | Hirai et al. | |
| 2017/0369756 A1 | | 12/2017 | Kodama et al. | |

FOREIGN PATENT DOCUMENTS

| | | |
|---|---|---|
| JP | 2004-518009 A | 6/2004 |
| JP | 2010-270256 A | 12/2010 |
| JP | 2014-012831 A | 1/2014 |
| JP | 2014-189736 A | 10/2014 |
| JP | 2014-189737 A | 10/2014 |
| JP | 2015-017212 A | 1/2015 |
| JP | 2015-052086 A | 3/2015 |
| JP | 2015-074669 A | 4/2015 |
| JP | 2015-218234 A | 12/2015 |
| JP | 2016-124931 A | 7/2016 |
| WO | WO 2013/163161 A1 | 12/2013 |

OTHER PUBLICATIONS

International Search Report for PCT/JP2017/017512 (PCT/ISA/210) dated Jun. 6, 2017.

* cited by examiner

*Primary Examiner* — Jane L Stanley
(74) *Attorney, Agent, or Firm* — Birch, Stewart, Kolasch & Birch, LLP

(57) ABSTRACT

The present invention relates to a viscometric properties improver capable of improving the fuel efficiency of an internal combustion engine, and an additive composition for a liquid coolant containing the viscometric properties improver. [1] A viscometric properties improver consisting of a compound (A) represented by the following formula (1) and a compound (B) represented by the following formula (2), and [2] an additive composition for a liquid coolant containing the same:

$$R^1O\text{---}(R^2O)_m\text{---}SO_3M \quad (1)$$

$$R^3O\text{---}SO_3M \quad (2)$$

wherein $R^1$ and $R^3$ are the same as or different from each other and each represent a linear or branched alkyl group or alkenyl group having 12 or more and 24 or less carbon atoms; $R^2$ represents an ethylene group or a propylene group; m represents an addition molar number of $R^2O$ of 1 or more and 15 or less; and M represents a cation or a hydrogen atom.

9 Claims, No Drawings

US 10,968,170 B2

VISCOMETRIC PROPERTIES IMPROVER

FIELD OF THE INVENTION

The present invention relates to a viscometric properties improver capable of improving the fuel efficiency of an internal combustion engine, and an additive composition for a liquid coolant containing the viscometric properties improver.

BACKGROUND OF THE INVENTION

Various materials have been known as a liquid coolant for cooling an internal combustion engine, such as an automobile engine, and among these, water is preferred due to the high cooling capability thereof as a liquid coolant for an engine. However, fresh water freezes at 0° C. Therefore, for enhancing the non-freezability of the liquid coolant, such a liquid coolant composition has been used that contains a glycol compound, such as ethylene glycol, as a base material, which is diluted with water to provide a necessary freezing temperature, to which various additives are added depending on necessity, for preventing deterioration of metals, rubber, resins, and the like used in an engine, a radiator, and the like.

However, the use of a glycol compound, such as ethylene glycol, causes a problem of considerable increase of the viscosity of the liquid coolant composition particularly at a low temperature. Accordingly, in the ordinary technique for improving the viscometric properties, the reduction in viscosity has been generally performed for enhancing the flowability at a low temperature.

However, the reduction in viscosity thins the thermal boundary layer between the liquid coolant and the cylinder bore wall, and facilitates the convection, thereby facilitating the withdrawal of heat from the cylinder bore wall, and as a result, another problem occurs that the cooling loss is increased to deteriorate the fuel efficiency.

On the other hand, in the case where the viscosity of the liquid coolant at a low temperature is increased by increasing the concentration of the glycol compound, such as ethylene glycol, for decreasing the cooling loss by lowering the heat radiation capability, a problem occurs that the cooling capability becomes insufficient at a high temperature, resulting in overheat.

As techniques for solving the aforementioned problem, for example, WO 2013/183161 (PTL 1) describes a liquid coolant composition for an internal combustion engine having a kinetic viscosity in the particular range, and a method for operating an internal combustion engine using the same, and describes that by making the kinetic viscosity of the liquid coolant composition in the particular range, the cooling loss at a low temperature can be decreased, and simultaneously the cooling capability at a high temperature can be retained.

JP 2010-270256 A (PTL 2) describes a liquid coolant composition containing water and a surfactant having a clouding point, and describes that by using the surfactant having a clouding point contained in the prescribed ratio, a liquid coolant composition having a high cooling capability and non-freezability can be obtained.

JP 2014-189736 A, JP 2014-189737 A, and JP 2015-74669 A (PTLs 3 to 5) describe a liquid coolant composition containing from 1 to 3 kinds of an alkyl ether and water and/or a water-soluble organic solvent, and describe that by further increasing the kinetic viscosity of the liquid coolant immediately after starting operation of an engine, the cooling loss can be decreased to raise the temperature of the engine rapidly to the optimum temperature, and the kinetic viscosity in the steady operation is further lowered to smooth the operation of the apparatus.

JP 2014-12831 (PTL 6) describes a liquid coolant composition containing a nonionic surfactant as a viscometric properties improver and a base material, having a kinetic viscosity of 8.5 mm²/sec or more at 25° C. and 2.0 mm²/sec or less at 100° C.

As described above, in the ordinary techniques, various viscometric properties improvers have been used as an additive for a liquid coolant, but for enhancing the fuel efficiency of an internal combustion engine, furthermore, it is necessary that the cooling loss at a low temperature is decreased by increasing the viscosity, so as to enhance the warm-up capability at a low temperature, while the cooling capability at a high temperature is retained with a small viscosity increase at a high temperature.

SUMMARY OF THE INVENTION

The present invention relates to a viscometric properties improver consisting of a compound (A) represented by the following formula (1) and a compound (B) represented by the following formula (2):

$$R^1O\text{-}(R^2O)_m\text{-}SO_3M \tag{1}$$

$$R^3O\text{---}SO_3M \tag{2}$$

wherein $R^1$ and $R^3$ are the same as or different from each other and each represent a linear or branched alkyl group or alkenyl group having 12 or more and 24 or less carbon atoms; $R^2$ represents an ethylene group or a propylene group; m represents an addition molar number of $R^2O$ of 1 or more and 15 or less; and M represents a cation or a hydrogen atom.

DETAILED DESCRIPTION OF THE INVENTION

The present invention relates to a viscometric properties improver capable of improving the fuel efficiency of an internal combustion engine, and an additive composition for a liquid coolant containing the viscometric properties improver.

The present inventors have found that by adding a particular alkyl or alkynyl ether sulfate salt and the like to the liquid coolant, (1) the shear viscosity of the liquid coolant can be controlled to a preferred range, the cooling loss at a low temperature can be reduced, and the cooling capability at a high temperature can be retained, and (2) such a property can be imparted to the liquid coolant that the liquid coolant is unlikely to suffer crystal deposition and/or gelation at a low temperature, as compared to the case where an ordinary viscometric properties improver is used, and consequently the fuel efficiency of an internal combustion engine can be largely enhanced.

Specifically, the present invention relates to the following items [1] and [2].

[1] A viscometric properties improver consisting of a compound (A) represented by the following formula (1) and a compound (B) represented by the following formula (2):

$$R^1O\text{-}(R^2O)_m\text{-}SO_3M \tag{1}$$

$$R^3O\text{---}SO_3M \tag{2}$$

wherein $R^1$ and $R^3$ are the same as or different from each other and each represent a linear or branched alkyl group or alkenyl group having 12 or more and 24 or less carbon atoms; $R^2$ represents an ethylene group or a propylene group; m represents an addition molar number of $R^2O$ of 1 or more and 15 or less; and M represents a cation or a hydrogen atom.

[2] An additive composition for a liquid coolant, containing the viscometric properties improver according to the item [1].

According to the present invention, a viscometric properties improver capable of improving the fuel efficiency of an internal combustion engine, and an additive composition for a liquid coolant containing the viscometric properties improver can be provided.

[Viscometric Properties Improver]

The viscometric properties improver of the present invention consists of a compound (A) represented by the following formula (1) (which may be hereinafter referred simply to a "compound (A)") and a compound (B) represented by the following formula (2) (which may be hereinafter referred simply to a "compound (B)"):

  (1)

  (2)

wherein $R^1$ and $R^3$ are the same as or different from each other and each represent a linear or branched alkyl group or alkenyl group having 12 or more and 24 or less carbon atoms; $R^2$ represents an ethylene group or a propylene group; m represents an addition molar number of $R^2O$ of 1 or more and 15 or less; and M represents a cation or a hydrogen atom.

In the description herein, the meanings of the terms, "viscometric properties improver", "additive composition for a liquid coolant", "liquid coolant", "liquid coolant composition", and "concentrated liquid coolant composition" are as follows.

The viscometric properties improver is a compound that is capable of providing two or more inflection points on the viscosity-temperature curve of the liquid coolant composition by adding the viscometric properties improver to the liquid coolant composition.

The additive composition for a liquid coolant is a composition that contains a viscometric properties improver for a liquid coolant.

The liquid coolant is a liquid medium that is used for decreasing the temperature of a target object to be cooled, such as water.

The liquid coolant composition is a composition that contains a liquid coolant having added thereto a glycol compound and various additives.

The concentrated liquid coolant composition is a concentrated product of a liquid coolant composition containing various additives and a medium. The concentrated liquid coolant composition is used for producing a liquid coolant by mixing and diluting with water while it can be used by itself as a liquid coolant.

According to the present invention, a liquid coolant that has a preferred shear viscosity at a low temperature and a high temperature can be prepared by adding the viscometric properties improver to the liquid coolant. In the present invention, the low temperature means approximately 25° C., and the high temperature means approximately 100° C.

Though the details of the functional mechanism of the effect of the viscometric properties improver of the present invention are not clear, it can be considered as follows. Specifically, it is considered that in the case where the viscometric properties improver consisting of the compound (A) and the compound (B) is added to a liquid coolant, (i) the compound (A) and the compound (B) are oriented in the liquid coolant composition, or (ii) form a composite with the base material of the liquid coolant, thereby forming a certain kind of a structure in the liquid coolant, and the structure can be modified through the temperature change, resulting in the improvement of the viscometric properties of the liquid coolant.

<Compound (A)>

The compound (A) is a polyoxyalkylene alkyl ether sulfate ester, a polyoxyalkylene alkenyl ether sulfate ester, or a salt thereof represented by the following formula (1).

The compound (A) suffices to contain any one of a polyoxyalkylene alkyl ether sulfate ester, a polyoxyalkylene alkyl ether sulfate ester salt, a polyoxyalkylene alkenyl ether sulfate ester, and a polyoxyalkylene alkenyl ether sulfate ester salt represented by the formula (1), and may contain two or more kinds thereof.

  (1)

In the formula, $R^1$ represents a linear or branched alkyl group or alkenyl group having 12 or more and 24 or less carbon atoms; $R^2$ represents an ethylene group or a propylene group; m represents an addition molar number of $R^2O$ of 1 or more and 15 or less; and M represents a cation or a hydrogen atom.

The alkyl group or the alkenyl group represented by $R^1$ in the formula (1) may be a linear or branched group, and is preferably a linear group from the standpoint that the shear viscosity at a low temperature is increased, and the shear viscosity at a high temperature is decreased, resulting in enhancement of the fuel efficiency of an internal combustion engine.

The number of carbon atoms of the alkyl group or the alkenyl group is 12 or more, preferably 16 or more, more preferably 18 or more, and further preferably 20 or more, and is 24 or less, and preferably 22 or less, from the same standpoint as above. Accordingly, the number of carbon atoms of the alkyl group or the alkenyl group is preferably 16 or more and 22 or less, more preferably 18 or more and 22 or less, and further preferably 20 or more and 22 or less.

Specific examples of $R^1$ include an alkyl group, such as a lauryl group, a myristyl group, a palmityl group, a margaryl group, an isostearyl group, a 2-heptylundecyl group, a stearyl group, an arachidyl group, a behenyl group, and a lignoceryl group; and an alkenyl group, such as an oleyl group, and from the same standpoint as above, a palmityl group, a stearyl group, and a behenyl group are preferred, and a behenyl group is more preferred.

$R^2O$ in the formula (1) is an ethyleneoxy group or a propyleneoxy group, and is preferably an ethyleneoxy group from the standpoint that a preferred shear viscosity is provided at a low temperature and a high temperature, resulting in enhancement of the fuel efficiency of an internal combustion engine.

m represents an addition molar number of $R^2O$, and is 1 or more, and preferably 2 or more, and is 15 or less, preferably 8 or less, more preferably 7 or less, further preferably 6 or less, still further preferably 5 or less, and still more further preferably 4 or less, from the standpoint that a preferred shear viscosity is provided at a low temperature and a high temperature, resulting in enhancement of the fuel efficiency of an internal combustion engine. Accordingly, m is 1 or more and 15 or less, preferably 1 or more and 8 or less, more preferably 1 or more and 7 or less, further preferably 1 or more and 5 or less, still further preferably 2 or more and 5 or less, and still more further preferably 2 or more and 4 or less.

m may have a distribution in some cases, i.e., the compound (A) may contain plural compounds having different addition molar numbers m of $R^2O$ in some cases, and a compound having m of 0 is not the compound (A) but is the compound (B) represented by the formula (2).

The amount of the components having m of from 1 to 5 is preferably 60% by mass or more, more preferably 70% by mass or more, and further preferably 80% by mass or more, and the amount of the components having m of from 2 to 4 is preferably 40% by mass or more, more preferably 50% by mass or more, and further preferably 55% by mass or more, all based on the viscometric properties improver.

The measurement of the addition molar number m and the distribution thereof may be performed, for example, according to the method described in examples.

M in the formula (1) represents a cation or a hydrogen atom.

In the case where M represents a cation, the compound represented by the formula (1) is a polyoxyalkylene alkyl ether sulfate salt or a polyoxyalkylene alkenyl ether sulfate salt. In this case, the compound represented by the formula (1) is strictly represented by the following formula (1-1).

$$R^1O\text{-}(R^2O)_m\text{-}SO_3^-M^+ \quad (1\text{-}1)$$

In the formula (1-1), $R^1$, $R^2$, and m have the same meanings as $R^1$, $R^2$, and m in the formula (1), and the preferred ranges thereof are also the same. $M^+$ represents a cation.

Examples of the cation represented by M include an alkali metal ion, such as a lithium ion, a sodium ion, and a potassium ion, an alkaline earth metal ion, such as a calcium ion, an ammonium ion, and an alkanolammonium ion, such as a triethanolammonium ion. Among these, M is preferably one or more kind selected from an alkali metal ion and an alkanolammonium ion, more preferably an alkali metal ion, and further preferably a sodium ion ($Na^+$) and a potassium ion ($K^+$), and is still further preferably a sodium ion ($Na^+$) from the standpoint that a preferred shear viscosity is provided at a low temperature and a high temperature, resulting in enhancement of the fuel efficiency of an internal combustion engine.

In the case where M is a divalent or higher valent cation, the cation may be present as a counter ion of the anion $-SO_3^-$, and for example, a divalent cation may be present in an amount of ½ of the amount of $-SO_3^-$.

In the case where M in the formula (1) is a hydrogen atom, the compound represented by the formula (1) is a polyoxyalkylene alkyl ether sulfate ester or a polyoxyalkylene alkenyl ether sulfate ester.

In one embodiment of the present invention, it is preferred to use the compound (A), in which $R^1$ is a linear alkyl group having 18 or more and 22 or less carbon atoms, $R^2O$ is an ethyleneoxy group, m is 1 or more and 8 or less, and M is a sodium ion or a potassium ion.

It is more preferred to use the compound (A), in which $R^1$ is a linear alkyl group having 20 or more and 22 or less carbon atoms, $R^2O$ is an ethyleneoxy group, m is 2 or more and 7 or less, and M is a sodium ion or a potassium ion, and it is further preferred to use the compound (A), in which $R^1$ is a linear alkyl group having a 20 or more and 22 or less carbon atoms, $R^2O$ is an ethyleneoxy group, m is 3 or more and 6 or less, and M is a sodium ion or a potassium ion.

Preferred specific examples of the compound (A) include one or more kind selected from $C_{18}H_{37}O-(CH_2CH_2O)_3-SO_3Na$, $C_{18}H_{37}O-(CH_2CH_2O)_3-SO_3K$, $C_{22}H_{45}O-(CH_2CH_2O)_4-SO_3Na$, and $C_{22}H_{45}O-(CH_2CH_2O)_4-SO_3K$.

The compound (A) may be used alone or as a mixture of two or more kinds thereof.

<Compound (B)>

The compound (B) is an alkyl sulfate ester, an alkenyl sulfate ester, or a salt thereof represented by the following formula (2).

The compound (B) suffices to contain any one of an alkyl sulfate ester, an alkyl sulfate ester salt, an alkenyl sulfate ester, and an alkenyl sulfate ester salt represented by the formula (2), and may contain two or more kinds thereof.

$$R^3O-SO_3M \quad (2)$$

In the formula, $R^3$ represents a linear or branched alkyl group or alkenyl group having 12 or more and 24 or less carbon atoms; and M represents a cation or a hydrogen atom.

$R^3$ in the formula (2) may be the same as or different from alkyl group or alkenyl group represented by $R^1$ in the formula (1).

The specific examples and the preferred examples of $R^3$ in the formula (2) are the same as for $R^1$ in the formula (1), the specific examples and the preferred examples of M in the formula (2) are the same as for M in the formula (1), and the descriptions therefor are omitted herein.

In the case where M in the formula (2) represents a cation, the compound represented by the formula (2) is an alkyl sulfate ester salt or an alkenyl sulfate ester salt. In this case, the compound represented by the formula (2) is strictly represented by the following formula (2-1).

$$R^3O-SO_3^-M^+ \quad (2\text{-}1)$$

In the formula (2-1), $R^3$ has the same meaning as $R^3$ in the formula (2), and the preferred range thereof is also the same. $M^+$ represents a cation.

In the case where M in the formula (2) is a hydrogen atom, the compound represented by the formula (2) is an alkyl sulfate ester or an alkenyl sulfate ester.

In one embodiment of the present invention, it is preferred to use the compound (B), in which $R^3$ is a linear alkyl group having 18 or more and 22 or less carbon atoms, and M is a sodium ion or a potassium ion, and it is more preferred to use the compound (B), in which $R^3$ is a linear alkyl group having 20 or more and 22 or less carbon atoms, and M is a sodium ion or a potassium ion.

Preferred specific examples of the compound (B) include one or more kind selected from $C_{18}H_{37}O-SO_3Na$, $C_{18}H_{37}O-SO_3K$, $C_{22}H_{45}O-SO_3Na$, and $C_{22}H_{45}O-SO_3K$.

The compound (B) may be used alone or as a mixture of two or more kinds thereof.

In the viscometric properties improver of the present invention, the mass ratio ((A)/(B)) of the compound (A) and the compound (B) is preferably 0.01 or more, more preferably 0.1 or more, further preferably 0.2 or more, and still further preferably 0.25 or more, and is preferably 50 or less, more preferably 20 or less, further preferably 10 or less, still further preferably 5 or less, still more further preferably 2 or less, and still more further preferably 0.5 or less, from the standpoint that a preferred shear viscosity is provided at a low temperature and a high temperature, resulting in enhancement of the fuel efficiency of an internal combustion engine.

[Additive Composition for Liquid Coolant]

The additive composition for a liquid coolant of the present invention contains the viscometric properties improver of the present invention.

The additive composition for a liquid coolant of the present invention suffices to contain at least the compound (A) and the compound (B), and may be prepared not only by adding the viscometric properties improver consisting of the compound (A) and the compound (B), but also by blending the compound (A) and the compound (B) separately.

In the additive composition for a liquid coolant of the present invention, the mass ratio ((A)/(B)) of the compound (A) and the compound (B) is preferably 0.01 or more, more preferably 0.1 or more, further preferably 0.2 or more, and still further preferably 0.25 or more, and is preferably 50 or less, more preferably 20 or less, further preferably 10 or less, still further preferably 5 or less, still more further preferably 2 or less, and still more further preferably 0.5 or less, from the standpoint that a preferred shear viscosity is provided at a low temperature and a high temperature, resulting in enhancement of the fuel efficiency of an internal combustion engine, as similar to the viscometric properties improver of the present invention.

In the additive composition for a liquid coolant of the present invention, the viscometric properties improver contained may be used alone or as a mixture of two or more kinds thereof.

The additive composition for a liquid coolant of the present invention preferably contains an additive that imparts various effects, such as non-freezability and anti-corrosion property, to the liquid coolant.

The additive composition for a liquid coolant of the present invention preferably further contains water from the standpoint of the workability in the preparation of the liquid coolant. The water is not particularly limited, and may be ion-exchanged water, reverse osmosis membrane-treated water (RO water), distilled water, pure water, and ultrapure water. Among these, ion-exchanged water is preferred from the standpoint of the availability, and the standpoint of the suppression of deposition of the hardness components in long-term storage and use as a liquid coolant.

The additive composition for a liquid coolant of the present invention may further contain one or more kind selected from an alkali metal salt and an alkali metal hydroxide other than the compound (A) and the compound (B) (which may be hereinafter referred to as a "component (C)").

The "alkali metal salt other than the compound (A) and the compound (B)" means alkali metal salts, from which ones corresponding to the compound (A) or the compound (B) are excluded.

The component (C) may be mixed with the compound (A) and/or the compound (B) in advance, and in this case, such an embodiment may be used that the alkali metal hydroxide is added to the compound (A) represented by the formula (1) and/or the compound (B) represented by the formula (2) in an excess amount exceeding the neutralization equivalent amount.

The alkali metal contained in the alkali metal salt and the alkali metal hydroxide is preferably one or more kind selected from lithium, sodium, and potassium, more preferably one or more kind selected from sodium and potassium, and further preferably potassium, from the standpoint that a preferred shear viscosity is provided at a low temperature and a high temperature, resulting in enhancement of the fuel efficiency of an internal combustion engine.

Preferred examples of the alkali metal salt other than the compound (A) and the compound (B) include one or more kind selected from an alkali metal salt of an inorganic acid or an organic acid, and an alkali metal salt of a triazole or a thiazole.

Examples of the alkali metal salt of an inorganic acid include alkali metal salts of nitrous acid, nitric acid, molybdic acid, hypochlorous acid, sulfuric acid, carbonic acid, hydrochloric acid, phosphoric acid, silicic acid, and boric acid.

Examples of the alkali metal salt of an organic acid include an alkali metal salt of an aromatic carboxylic acid, such as benzoic acid, p-toluic acid, and p-tert-butylbenzoic acid; an alkali metal salt of an aliphatic monocarboxylic acid, such as pentanoic acid, hexanoic acid, heptanoic acid, octanoic acid, 2-ethylhexanoic acid, nonanoic acid, decanoic acid, undecanoic acid, dodecanoic acid, and oleic acid; and an alkali metal salt of an aliphatic polycarboxylic acid, such as azelaic acid, sebacic acid, undecanedioic acid, dodecanedioic acid, and citric acid.

Examples of the alkali metal salt of a triazole or a thiazole include an alkali metal salt of benzotriazole.

Among the alkali metal salts, an alkali metal salt of an aliphatic polycarboxylic acid is preferred, an alkali metal salt of sebacic acid is more preferred, and potassium sebacate is further preferred, from the standpoint that the shear viscosity of the liquid coolant composition is in a preferred range at a low temperature and a high temperature, resulting in enhancement of the fuel efficiency of an internal combustion engine.

The alkali metal hydroxide used in the additive composition for a liquid coolant of the present invention is not particularly limited, and preferred examples thereof include one or more kind selected from lithium hydroxide, sodium hydroxide, and potassium hydroxide. Among the alkali metal hydroxides, potassium hydroxide is preferred from the standpoint that the shear viscosity of the liquid coolant composition is in a preferred range at a low temperature and a high temperature, resulting in enhancement of the fuel efficiency of an internal combustion engine, and the standpoint of the storage stability in the case where water is contained.

The additive composition for a liquid coolant of the present invention can be obtained by mixing the compound (A), the compound (B), and the other components, and heating and stirring the mixture depending on necessity. The order of blending the components is not particularly limited.

(Contents of Components)

The total content of the compound (A) and the compound (B) of the additive composition for a liquid coolant of the present invention is preferably 1% by mass or more based on the additive composition for a liquid coolant from the standpoint that the shear viscosity of the liquid coolant composition is in a preferred range at a low temperature and a high temperature, resulting in enhancement of the fuel efficiency of an internal combustion engine, and is preferably 5% by mass or more, more preferably 10% by mass or more, further preferably 50% by mass or more, and still further preferably 100%, from the standpoint of the transport efficiency and the storage efficiency. The total content of the compound (A) and the compound (B) is preferably 90% by mass or less, more preferably 50% by mass or less, further preferably 30% by mass or less, and still further preferably 20% by mass or less, from the standpoint of the workability in the preparation of the liquid coolant.

The compound (A) and the compound (B) are preferably in such a form that both the compounds are uniformly mixed or uniformly dispersed to make an integrated form from the standpoint of providing a preferred shear viscosity as a liquid coolant, and the individual compounds or plural mixtures thereof prepared in advance with different ratios may be added to the liquid coolant in such a mass ratio that provides the target shear viscosity.

The content of water in the additive composition for a liquid coolant of the present invention is preferably 1% by mass or more, more preferably 10% by mass or more, further preferably 50% by mass or more, and still further preferably 80% by mass or more, based on the additive composition for a liquid coolant, from the standpoint of the workability in the preparation of the liquid coolant, and is preferably 95% by mass or less, more preferably 90% by mass or less, further preferably 50% by mass or less, and still further preferably 20% by mass or less, from the standpoint of the transport efficiency and the storage efficiency.

The content of the alkali metal salt and/or the alkali metal hydroxide other than the compound (A) and the compound (B) is preferably 0.01% by mass or more, more preferably 0.02% by mass or more, further preferably 0.05% by mass or more, and still further preferably 0.1% by mass or more, and is preferably 1% by mass or less, more preferably 0.5% by mass or less, further preferably 0.4% by mass or less, and still further preferably 0.3% by mass or less, based on the additive composition for a liquid coolant, from the standpoint that the shear viscosity of the liquid coolant composition is in a preferred range at a low temperature and a high temperature in relation to the viscometric properties improver used, resulting in enhancement of the fuel efficiency of an internal combustion engine, and the standpoint of the storage stability in the case where water is contained.

With the alkali metal salt and/or the alkali metal hydroxide other than the compound (A) and the compound (B) contained, the pH of the additive composition for a liquid coolant can be controlled, and the pH thereof at 25° C. is preferably 8 or more, and more preferably 9 or more, and is preferably 11 or less, and more preferably 10 or less, from the standpoint of the storage stability in the case where water is contained.

The additive composition for a liquid coolant of the present invention contains the compound (A) and the compound (B) as components of the viscometric properties improver as aforementioned, and thereby the shear viscosity of the liquid coolant can be in a preferred range, resulting in enhancement of the fuel efficiency of an internal combustion engine.

The increase of the shear viscosity at 25° C. can be achieved by a method of increasing the content of the viscometric properties improver, a method of controlling the content of the alkali metal salt and/or the alkali metal hydroxide, and the like, and the decrease of the shear viscosity at 100° C. can be achieved by a method decreasing the content of the viscometric properties improver, a method of controlling the content of the alkali metal salt and/or the alkali metal hydroxide, and the like.

(Rust Inhibitor and the Like)

The additive composition for a liquid coolant of the present invention may contain at least one kind of a rust inhibitor in such a range that does not influence the viscosity of the liquid coolant, for effectively suppressing corrosion of metals used in the liquid coolant flow path of the engine. Examples of the rust inhibitor include one kind and a mixture of two or more kinds selected from phosphoric acid and a salt thereof, an aliphatic carboxylic acid and a salt thereof, an aromatic carboxylic acid and a salt thereof, a triazole compound, a thiazole compound, a silicate salt, a nitrate salt, a nitrite salt, a borate salt, a molybdate salt, and an amine salt. The content of the rust inhibitor is preferably from 0 to 100 parts by mass, more preferably from 10 to 80 parts by mass, further preferably from 20 to 50 parts by mass, and still further preferably from 25 to 40 parts by mass, per 100 parts by mass of the total mass of the compound (A) and the compound (B) in the additive composition for a liquid coolant.

The additive composition for a liquid coolant of the present invention may further have blended therein an additional additive in such a range that does not impair the effects of the present invention. Examples of the additional additive include a thickener, a pH modifier, an anti-foaming agent, a colorant, and a bittering agent.

The thickener is preferably a polymer polysaccharide, a water-soluble resin, or the like. Examples of the polymer polysaccharide include hydroxyethyl cellulose, carboxymethyl cellulose, and xanthan gum, and examples of the water-soluble resin include polyvinyl alcohol and gum arabic.

Examples of the anti-foaming agent include a silicone series compounds and a polyether series compounds.

The total amount of the additional additives blended is generally 10 parts by mass or less, and preferably 5 parts by mass or less, per 100 parts by mass of the additive composition for a liquid coolant.

The additive composition for a liquid coolant of the present invention may be used for a liquid coolant of an internal combustion engine and a battery stack of vehicles, boats and ships, aircrafts, electric generators, heating and cooling systems, and the like. Among these, the additive composition for a liquid coolant is preferably used for a liquid coolant of an internal combustion engine.

The internal combustion engine herein means an engine, in which a fuel is combusted in a cylinder, and the combustion gas is directly used as a working fluid to perform work with the heat energy thereof, and examples thereof include a piston engine and a rotary engine as a space displacement type, and a gas turbine engine and a jet engine as a fluid flow type. Among these, the internal combustion engine is preferably a piston engine or a rotary engine for an automobile.

[Liquid Coolant and Liquid Coolant Composition]

The amount of the additive composition for a liquid coolant of the present invention added to a liquid coolant is preferably 0.01% by mass or more, more preferably 0.02% by mass or more, further preferably 0.03% by mass or more, still further preferably 0.05% by mass or more, still more further preferably 0.15% by mass or more, still more further preferably 0.25% by mass or more, and is preferably 10% by mass or less, more preferably 5% by mass or less, further preferably 3% by mass or less, still further preferably 2% by mass or less, still more further preferably 1% by mass or less, and still more further preferably 0.5% by mass or less, in terms of total amount of the compound (A) and the compound (B) per 100 parts by mass of the liquid coolant composition, from the standpoint that the shear viscosity of the liquid coolant composition is in a preferred range at a low temperature and a high temperature, resulting in enhancement of the fuel efficiency of an internal combustion engine.

The liquid coolant containing the additive composition for a liquid coolant of the present invention preferably has a shear viscosity at 25° C. of 5 mPa·s or more from the standpoint of suppressing the cooling loss at a low temperature, and preferably has a shear viscosity at 25° C. of 200 mPa·s or less from the standpoint of reducing the load to a water pump for cooling an internal combustion engine and suppressing deterioration of the fuel efficiency of the internal combustion engine. In these standpoints, the shear viscosity at 25° C. of the liquid coolant is preferably from 5 to 200 mPa·s, more preferably from 8 to 100 mPa·s, further preferably from 10 to 80 mPa·s, still further preferably from 12 to 60 mPa·s, and still more further preferably from 15 to 50 mPa·s.

The liquid coolant containing the additive composition for a liquid coolant of the present invention preferably has a shear viscosity at 100° C. of 2 mPa·s or less, more preferably from 0.5 to 2.0 mPa·s, further preferably from 0.8 to 1.8 mPa·s, and still further preferably from 1.0 to 1.6 mPa·s, from the standpoint of retaining the cooling capability at a high temperature and suppressing overheat.

The base material of the liquid coolant for an internal combustion engine may contain at least one kind of an alcohol compound selected from an alcohol, such as a monohydric alcohol, a dihydric alcohol, and a trihydric alcohol, and a glycol monoalkyl ether, and/or water.

The liquid coolant for an internal combustion engine preferably contains a base material having non-freezability, and the base material thereof may be water alone in the case where non-freezability is not necessary.

Examples of the monohydric alcohol include a monohydric alcohol preferably having from 1 to 8 carbon atoms, more preferably having from 1 to 3 carbon atoms, such as methanol, ethanol, propanol, butanol, pentanol, hexanol, heptanol, and octanol, and include one kind and a mixture of two or more kinds selected from these compounds.

Examples of the dihydric alcohol include a dihydric alcohol preferably having from 2 to 8 carbon atoms, more preferably having from 2 to 3 carbon atoms, such as ethylene glycol, diethylene glycol, triethylene glycol, propylene glycol, 1,3-propanediol, 1,4-butanediol, 1,3-butanediol, 1,5-pentanediol, and hexylene glycol, and include one kind and a mixture of two or more kinds selected from these compounds.

Examples of the trihydric alcohol include a trihydric alcohol preferably having from 3 to 6 carbon atoms, more preferably 3 carbon atoms, such as glycerin, trimethylolethane, trimethylolpropane, 5-methyl-1,2,4-heptanetriol, and 1,2,6-hexanetriol, and include one kind and a mixture of two or more kinds selected from these compounds.

The number of carbon atoms of the alkyl group of the glycol monoalkyl ether is preferably from 1 to 4, and more preferably from 1 to 2, and the number of carbon atoms of the glycol thereof is preferably from 2 to 6, and more preferably 2. Examples of the glycol monoalkyl ether include ethylene glycol monomethyl ether, diethylene glycol monomethyl ether, triethylene glycol monomethyl ether, tetraethylene glycol monomethyl ether, ethylene glycol monoethyl ether, diethylene glycol monoethyl ether, triethylene glycol monoethyl ether, tetraethylene glycol monoethyl ether, ethylene glycol monobutyl ether, diethylene glycol monobutyl ether, triethylene glycol monobutyl ether, and tetraethylene glycol monobutyl ether, and include one kind and a mixture of two or more kinds selected from these compounds.

Among the aforementioned base materials, one kind or two or more kinds selected from ethylene glycol, propylene glycol, 1,3-propanediol, and water are preferred, and ethylene glycol and water are more preferably contained, from the standpoint of the handleability, the cost, and the availability.

The water used as the base material is preferably ion-exchanged water.

(Compositional Formulation)

The content of the base material in 100 parts by mass of a liquid coolant, particularly a liquid coolant for an internal combustion engine, is preferably 50 parts by mass or more, more preferably 75 parts by mass or more, further preferably 80 parts by mass or more, and still further preferably 90 parts by mass or more, from the standpoint the function as a liquid coolant.

The content of the alcohol compound, preferably ethylene glycol, in 100 parts by mass of a liquid coolant, particularly a liquid coolant for an internal combustion engine, is preferably from 1 to 99.85 parts by mass, more preferably from 10 to 95 parts by mass, further preferably from 25 to 89 parts by mass, and still further preferably from 25 to 74 parts by mass, from the standpoint of the non-freezability.

The content of water in 100 parts by mass of a liquid coolant, particularly a liquid coolant for an internal combustion engine, is preferably from 0.1 to 99.85 parts by mass, more preferably from 0.3 to 95 parts by mass, further preferably from 10 to 74 parts by mass, and still further preferably from 25 to 74 parts by mass.

In the case where the base material contains water and the alcohol compound, the blending ratio of water and the alcohol compound may be arbitrarily controlled in consideration of the non-freezability and the inflammability. The mass ratio of water and the alcohol compound in the base material is preferably from 20/80 to 90/10 (water/alcohol compound), and more preferably from 40/60 to 75/25, from the standpoint of preventing an inflammation point from being generated.

The liquid coolant, particularly the liquid coolant for an internal combustion engine, preferably obtained by mixing the base material, the viscometric properties improver of the present invention, a rust inhibitor depending on necessity, and an additional additive other than a rust inhibitor depending on necessity. Examples of the additional additive include a pH modifier, an anti-foaming agent, and a colorant, which may be appropriately added in such a range that does not influence the kinetic viscosity and the like. The liquid coolant, particularly the liquid coolant for an internal combustion engine, is preferably obtained in such a manner that the components are mixed and then dissolved by heating to preferably 60° C. or more, and more preferably 80° C. or more, and preferably 100° C. or less, and stirring depending on necessity, and the mixture is then cooled to room temperature (20° C.).

In relation to the aforementioned embodiments, the present invention further provides the viscometric properties improvers and the additive compositions for a liquid coolant shown below.

<1> A viscometric properties improver consisting of a compound (A) represented by the following formula (1) and a compound (B) represented by the following formula (2):

(1)

(2)

wherein $R^1$ and $R^3$ are the same as or different from each other and each represent a linear or branched alkyl group or alkenyl group having 12 or more and 24 or less carbon atoms; $R^2$ represents an ethylene group or a propylene group; m represents an addition molar number of $R^2O$ of 1 or more and 15 or less; and M represents a cation or a hydrogen atom.

<2> The viscometric properties improver according to the item <1>, wherein the number of carbon atoms of the alkyl group or the alkenyl group represented by $R^1$ in the formula (1) is preferably 16 or more, more preferably 18 or more, and further preferably 20 or more, and is preferably 22 or less.

<3> The viscometric properties improver according to the item <1> or <2>, wherein m in the formula (1) is preferably 2 or more, and is preferably 8 or less, more preferably 7 or less, further preferably 6 or less, still further preferably 5 or less, and still more further preferably 4 or less.

<4> The viscometric properties improver according to any one of the items <1> to <3>, wherein the amount of the components having m in the formula (1) of from 1 to 5 is preferably 60% by mass or more, more preferably 70% by mass or more, and further preferably 80% by mass or more, and the amount of the components having m of from 2 to 4 is preferably 40% by mass or more, more preferably 50% by mass or more, and further preferably 55% by mass or more.

<5> The viscometric properties improver according to any one of the items <1> to <4>, wherein the compound (A) is preferably a compound, in which $R^1$ is a linear alkyl group having 18 or more and 22 or less carbon atoms, $R^2O$ is an ethyleneoxy group, m is 1 or more and 8 or less, and M is a sodium ion or a potassium ion, more preferably a compound, in which $R^1$ is a linear alkyl group having 20 or more and 22 or less carbon atoms, $R^2O$ is an ethyleneoxy group, m is 2 or more and 7 or less, and M is a sodium ion or a potassium ion, and further preferably a compound, in which $R^1$ is a linear alkyl group having 20 or more and 22 or less carbon atoms, $R^2O$ is an ethyleneoxy group, m is 3 or more and 6 or less, and M is a sodium ion or a potassium ion.

<6> The viscometric properties improver according to any one of the items <1> to <5>, wherein the compound (A) is one or more kind selected from $C_{18}H_{37}O—(CH_2CH_2O)_3—SO_3Na$, $C_{18}H_{37}O—(CH_2CH_2O)_3—SO_3K$, $C_{22}H_{45}O—(CH_2CH_2O)_4—SO_3Na$, and $C_{22}H_{45}O—(CH_2CH_2O)_4—SO_3K$.

<7> The viscometric properties improver according to any one of the items <1> to <6>, wherein the number of carbon atoms of the alkyl group or the alkenyl group represented by $R^3$ in the formula (2) is preferably 16 or more, more preferably 18 or more, and further preferably 20 or more, and is preferably 22 or less.

<8> The viscometric properties improver according to any one of the items <1> to <7>, wherein the compound (B) is one or more kind selected from $C_{18}H_{37}O—SO_3Na$, $C_{18}H_{37}O—SO_3K$, $C_{22}H_{45}O—SO_3Na$, and $C_{22}H_{45}O—SO_3K$.

<9> The viscometric properties improver according to any one of the items <1> to <8>, wherein the mass ratio ((A)/(B)) of the compound (A) and the compound (B) is preferably 0.01 or more, more preferably 0.1 or more, further preferably 0.2 or more, and still further preferably 0.25 or more, and is preferably 50 or less, more preferably 20 or less, further preferably 10 or less, still further preferably 5 or less, still more further preferably 2 or less, and still more further preferably 0.5 or less.

<10> An additive composition for a liquid coolant, containing the viscometric properties improver according to any one of the items <1> to <9>.

<11> The additive composition for a liquid coolant according to the item <10>, wherein the mass ratio ((A)/(B)) of the compound (A) and the compound (B) is preferably 0.01 or more, more preferably 0.1 or more, further preferably 0.2 or more, and still further preferably 0.25 or more, and is preferably 50 or less, more preferably 20 or less, further preferably 10 or less, still further preferably 5 or less, still more further preferably 2 or less, and still more further preferably 0.5 or less.

<12> The additive composition for a liquid coolant according to the item <10> or <11>, further containing water.

<13> The additive composition for a liquid coolant according to any one of the items <10> to <12>, further containing one or more kind selected from an alkali metal salt and an alkali metal hydroxide other than the compound (A) and the compound (B).

<14> The additive composition for a liquid coolant according to any one of the items <10> to <13>, wherein the alkali metal salt other than the compound (A) and the compound (B) is one or more kind selected from an alkali metal salt of an inorganic acid or an organic acid, and an alkali metal salt of a triazole or a thiazole, preferably an alkali metal salt of an aliphatic polycarboxylic acid, more preferably an alkali metal salt of sebacic acid, and further preferably potassium sebacate, and the alkali metal hydroxide is one or more kind selected from lithium hydroxide, sodium hydroxide, and potassium hydroxide.

<15> The additive composition for a liquid coolant according to any one of the items <10> to <14>, wherein the total content of the compound (A) and the compound (B) is preferably 1% by mass or more, more preferably 5% by mass or more, further preferably 10% by mass or more, still further preferably 50% by mass or more, and still more further preferably 100%, and is preferably 90% by mass or less, more preferably 50% by mass or less, further preferably 30% by mass or less, and still further preferably 20% by mass or less.

<16> The additive composition for a liquid coolant according to any one of the items <10> to <15>, wherein the content of water is preferably 1% by mass or more, more preferably 10% by mass or more, further preferably 50% by mass or more, and still further preferably 80% by mass or more, and is preferably 95% by mass or less, more preferably 90% by mass or less, further preferably 50% by mass or less, and still further preferably 20% by mass or less.

<17> The additive composition for a liquid coolant according to any one of the items <10> to <16>, wherein the content of the alkali metal salt and/or the alkali metal hydroxide other than the compound (A) and the compound (B) is preferably 0.01% by mass or more, more preferably 0.02% by mass or more, further preferably 0.05% by mass or more, and still further preferably 0.1% by mass or more, and is preferably 1% by mass or less, more preferably 0.5% by mass or less, further preferably 0.4% by mass or less, and still further preferably 0.3% by mass or less.

<18> The additive composition for a liquid coolant according to any one of the items <10> to <17>, containing at least the compound (A) and the compound (B) blended therein.

<19> The additive composition for a liquid coolant according to any one of the items <10> to <18>, wherein the liquid coolant is a liquid coolant for an internal combustion engine.

<20> A liquid coolant composition containing the viscometric properties improver according to any one of the items <1> to <9> or the additive composition for a liquid coolant according to any one of the items <10> to <19>.

<21> A method for cooling an internal combustion engine, including using the liquid coolant composition according to the item <20>.

<22> A method for operating an internal combustion engine, including using the liquid coolant composition according to the item <20> as a liquid coolant for an internal combustion engine.

EXAMPLES

In Synthesis Examples, Working Examples, Comparative Examples, and Application Examples shown below, the percentage means the percentage by mass unless otherwise indicated.

Synthesis Example 1

(Synthesis of Compound (A))

Ethoxylate of 1-docosanol (produced by Tokyo Kasei Kogyo Co., Ltd.) (average addition molar number of ethylene oxide: 4.0) was distilled at 250° C. under reduced pressure of 133.3 Pa to remove the unreacted alcohol, and subjected to sulfation reaction with sulfamic acid (molar ratio of sulfamic acid/ethoxylate: 1.10) at a reaction temperature of 110° C.

Polyoxyethylene behenyl ether sulfate sodium salt ($C_{22}H_{45}O$—$(CH_2CH_2O)_m$—$SO_3Na$, Compound (A)) was synthesized in such a manner that 256 g of the resulting polyoxyethylene behenyl ether sulfate was neutralized with a 48% sodium hydroxide aqueous solution, then heated to 80° C. with supplying nitrogen to perform deammoniation, and the concentration of the polyoxyethylene behenyl ether sulfate sodium salt was controlled to 13% by mass with water.

<Measurement Method of Addition Molar Number of Ethylene Oxide>

The ethoxylate of 1-docosanol as the intermediate in Synthesis Example 1, from which the unreacted alcohol had been removed, was measured with chromatography under the following condition, and from the area ratios of the peaks in the resulting chromatogram, the distribution of the addition molar number of ethylene oxide of the resulting polyoxyethylene behenyl ether sulfate sodium salt (i.e., m in the formula (1)) was measured. The results are shown in Table 1.

(Measurement Condition)

Measuring equipment: Agilent 6890N (gas chromatography, produced by Agilent Technologies, Inc.)

Column: DB-1ht (produced by Agilent Technologies, Inc.) (length: 30 m, inner diameter: 0.25 mm, membrane thickness: 0.10 μm)

Carrier gas: He (constant flow mode)

Split ratio: 50/1

Detector: FID

Injection port temperature: 330° C.

Detector temperature: 330° C.

Measurement temperature condition: starting from 100° C., raised at 10° C./min, and retained at 380° C. for 27 minutes Detection sensitivity:

Uptake rate: 20 Hz

Minimum peak width: 0.01 min

Injection amount: 1 μL (split method)

Quantitative determination of components (% by mass): With respect to the total area of all the peaks as 100, the content of the components were calculated from the area ratios of the peaks corresponding to the components.

TABLE 1

Distribution of m in Compound (A)

| $R^1$ | $R^2$ | m | M | Content (% by mass) |
|---|---|---|---|---|
| behenyl group | ethylene group | 1 | $Na^+$ | 14.7 |
| behenyl group | ethylene group | 2 | $Na^+$ | 20.5 |
| behenyl group | ethylene group | 3 | $Na^+$ | 21.7 |
| behenyl group | ethylene group | 4 | $Na^+$ | 17.2 |
| behenyl group | ethylene group | 5 | $Na^+$ | 11.4 |
| behenyl group | ethylene group | 6 | $Na^+$ | 7.8 |
| behenyl group | ethylene group | 7 | $Na^+$ | 4.0 |
| behenyl group | ethylene group | 8 | $Na^+$ | 1.7 |
| behenyl group | ethylene group | 9 | $Na^+$ | 0.7 |
| behenyl group | ethylene group | 10 | $Na^+$ | 0.3 |

It is understood from Table 1 that the addition molar number m of ethylene oxide of the resulting polyoxyethylene behenyl ether sulfate sodium salt is from 1 to 10, the amount of the components having m of from 1 to 5 is 85.5% by mass, and the amount of the components having m of from 2 to 4 is 59.4% by mass.

Synthesis Example 2

(Synthesis of Compound (B))

1-Docosanol (produced by Tokyo Kasei Kogyo Co., Ltd., known as behenyl alcohol) was subjected to sulfation reaction with sulfamic acid (molar ratio of sulfamic acid/1-docosanol: 1.10) at a reaction temperature of 110° C.

Behenyl sulfate sodium salt ($C_{22}H_{45}O$—$SO_3Na$, Compound (B)) was synthesized in such a manner that 256 g of the resulting behenyl sulfate was neutralized with a 48% sodium hydroxide aqueous solution, then heated to 80° C. with supplying nitrogen to perform deammoniation, and the concentration of the behenyl sulfate sodium salt was controlled to 13% by mass with water.

Examples 1 to 5 and Comparative Examples 1 to 3

(Production of Additive Compositions for Liquid Coolant 1 to 8)

The viscometric properties improver containing the compound (A) and the compound (B), ion-exchanged water, and thickeners were blended to make effective ingredients shown in Table 2, and thus the additive compositions for a liquid coolant 1 to 8 were produced.

In Table 2, thickeners 1 and 2 are as follows.

Thickener 1: xanthan gum (produced by Tokyo Kasei Kogyo Co., Ltd.)

Thickener 2: polyvinyl alcohol (produced by Kuraray Co., Ltd., Kuraray Poval PVA-117, polymerization degree: 1,700)

TABLE 2

|  |  | Example | | | | | Comparative Example | | |
|---|---|---|---|---|---|---|---|---|---|
|  |  | 1 | 2 | 3 | 4 | 5 | 1 | 2 | 3 |
| No. of additive composition for liquid coolant | | 1 | 2 | 3 | 4 | 5 | 6 | 7 | 8 |
| Compositional formulation | Compound (A) (% by mass) | 1.25 | 2.50 | 5.00 | 8.75 | 9.50 | — | — | — |
| | Compound (B) (% by mass) | 8.75 | 7.50 | 5.00 | 1.25 | 0.50 | 10.00 | — | — |
| | Thickener 1 (% by mass) | — | — | — | — | — | — | 15.00 | — |
| | Thickener 2 (% by mass) | — | — | — | — | — | — | — | 100 |
| | Ion-exchanged water (% by mass) | 90.00 | 90.00 | 90.00 | 90.00 | 90.00 | 90.00 | 85.00 | — |
| Compound (A)/Compound (B) | | 0.14 | 0.33 | 1.00 | 7.00 | 19.00 | — | — | — |

Application Examples 1 to 5 and Comparative Application Examples 1 to 4

(1) Production of Concentrated Liquid Coolant Composition

Sebacic acid (produced by Kokura Synthetic Industries, Ltd.), potassium hydroxide (produced by Osaka Soda Co., Ltd., a 47% diluted product), ethylene glycol (produced by Maruzen Petrochemical Co., Ltd.), and water (pure water of 1 μS/cm or less produced with Pure Water System G-10DST-SET, produced by Organo Corporation) were mixed at room temperature to provide a concentrated liquid coolant composition having effective ingredients at mixing of 4% by mass of sebacic acid, 2% by mass of potassium hydroxide, 90% by mass of ethylene glycol, and 4% by mass of water.

(2) Production of Liquid Coolant Composition

The concentrated liquid coolant composition obtained in the item (1) above, the additive compositions for a liquid coolant 1 to 8 obtained in Examples 1 to 5 and Comparative Examples 1 to 3, and water were mixed at the ratios shown in Table 3 to provide liquid coolant compositions. The resulting liquid coolant compositions were measured for the shear viscosity in the following manner. The results are shown in Table 3.

<Measurement of Shear Viscosity>

The liquid coolant compositions prepared in Application Examples and Comparative Application Examples each were allowed to stand in a thermostat chamber set at the measurement temperature for 1 hour, and then measured for the shear viscosity with a rheometer, produced by Anton Paar GmbH (Model MCR-302) and an attachment (CP50-1) at a rotation rate of 22 per second or 100 per second (measurement time: 5 second, measurement temperature: 25° C. or 100° C.).

It is understood from Table 3 that the liquid coolants (Application Examples 1 to 5) containing the viscometric properties improver and the additive composition for a liquid coolant of the present invention has a shear viscosity at a low temperature (25° C.) of 5 mPa·s or more, particularly 10 mPa·s or more, and thus can reduced the load to an internal combustion engine and the like, and can suppress deterioration of the fuel efficiency of the internal combustion engine. Furthermore, the shear viscosity at a high temperature (100° C.) thereof is 2 mPa or less, particularly 1.6 mPa·s or less, and thus the cooling capability at a high temperature is retained to prevent overheat.

INDUSTRIAL APPLICABILITY

The viscometric properties improver and the additive composition for a liquid coolant of the present invention can be favorably used for cooling an internal combustion engine and a battery stack of automobiles, vehicles, such as working vehicles (e.g., trucks and heavy machineries), boats and ships, aircrafts, electric generators, heating and cooling systems, and the like.

The invention claimed is:

1. An additive composition for a liquid coolant, comprising
a compound (A) represented by the following formula (1) and a compound (B) represented by the following formula (2):

$$R^1O\text{-}(R^2O)_m\text{-}SO_3M \quad (1)$$

$$R^3O\text{-}SO_3M \quad (2)$$

TABLE 3

|  |  | Application Example | | | | | Comparative Application Example | | | |
|---|---|---|---|---|---|---|---|---|---|---|
|  |  | 1 | 2 | 3 | 4 | 5 | 1 | 2 | 3 | 4 |
| Compositional formulation (% by mass) | Concentrated liquid coolant composition | 51.0 | 51.0 | 51.0 | 51.0 | 51.0 | 51.0 | 51.0 | 51.0 | 51.0 |
| | Water | 45.0 | 45.0 | 45.0 | 45.0 | 45.0 | 49.0 | 45.0 | 46.33 | 48.6 |
| | Additive composition for liquid coolant 1 | 4.0 | — | — | — | — | — | — | — | — |
| | Additive composition for liquid coolant 2 | — | 4.0 | — | — | — | — | — | — | — |
| | Additive composition for liquid coolant 3 | — | — | 4.0 | — | — | — | — | — | — |
| | Additive composition for liquid coolant 4 | — | — | — | 4.0 | — | — | — | — | — |
| | Additive composition for liquid coolant 5 | — | — | — | — | 4.0 | — | — | — | — |
| | Additive composition for liquid coolant 6 | — | — | — | — | — | — | 4.0 | — | — |
| | Additive composition for liquid coolant 7 | — | — | — | — | — | — | — | 2.67 | — |
| | Additive composition for liquid coolant 8 | — | — | — | — | — | — | — | — | 0.4 |
| Evaluation result | Shear viscosity (mPa · s, 25° C., 22 per second) | 26.0 | 43.0 | 17.0 | 10.0 | 13.0 | 3.6 | 4.5 | 43.0 | 12.0 |
| | Shear viscosity (mPa · s, 100° C., 100 per second) | 1.2 | 1.3 | 1.5 | 1.4 | 1.2 | 0.9 | 1.2 | 10.0 | 2.6 | wherein $R^1$ and $R^3$ are the same as or different from each other and each represent a linear or branched alkyl group or alkenyl group having 16 or more and 24 or less carbon atoms; $R^2$ represents an ethylene group or a propylene group; m represents an addition molar number of $R^2O$ of 1 or more and 15 or less; and M represents a cation or a hydrogen atom, a non-freezability additive, an anticorrosion additive, and a rust inhibitor, and water.

2. The additive composition for a liquid coolant according to claim 1, wherein a mass ratio ((A)/(B)) of the compound (A) and the compound (B) is 0.01 or more and 50 or less.

3. The additive composition for a liquid coolant according to claim 1, further comprising ion-exchanged water.

4. The additive composition for a liquid coolant according to claim 1, further comprising one or more kind selected from an alkali metal salt and an alkali metal hydroxide other than the compound (A) and the compound (B).

5. The additive composition for a liquid coolant according to claim 1, wherein the liquid coolant is a liquid coolant for an internal combustion engine.

6. The additive composition for a liquid coolant according to claim 1, wherein the compound (A) is one or more kind selected from $C_{18}H_{37}O$—$(CH_2CH_2O)_3$—$SO_3Na$, $C_{18}H_{37}O$—$(CH_2CH_2O)_3$—$SO_3K$, $C_{22}H_{45}O$—$(CH_2CH_2O)_4$—$SO_3Na$, and $C_{22}H_{45}O$—$(CH_2CH_2O)_4$—$SO_3K$.

7. The additive composition for a liquid coolant according to claim 1, wherein the compound (B) is one or more kind selected from $C_{18}H_{37}O$—$SO_3Na$, $C_{18}H_{37}O$—$SO_3K$, $C_{22}H_{45}O$—$SO_3Na$, and $C_{22}H_{45}O$—$SO_3K$.

8. A liquid coolant, comprising the additive composition according to claim 1, wherein the shear viscosity at 25° C. of the liquid coolant is from 5 to 200 mPa·s and the shear viscosity at 100° C. of the liquid coolant is 2 mPa·s or less.

9. The liquid coolant according to claim 8, wherein the compound (A) is at least one compound selected from $C_{18}H_{37}O$—$(CH_2CH_2O)_3$—$SO_3Na$, $C_{18}H_{37}O$—$(CH_2CH_2O)_3$—$SO_3K$, $C_{22}H_{45}O$—$(CH_2CH_2O)_4$—$SO_3Na$, and $C_{22}H_{45}O$—$(CH_2CH_2O)_4$—$SO_3K$, and the compound (B) is at least one compound selected from $C_{18}H_{37}O$—$SO_3Na$, $C_{18}H_{37}O$—$SO_3K$, $C_{22}H_{45}O$—$SO_3Na$, and $C_{22}H_{45}O$—$SO_3K$.

* * * * *